(12) United States Patent
Lang

(10) Patent No.: US 8,455,515 B2
(45) Date of Patent: Jun. 4, 2013

(54) SUBSTITUTED 4-PHENYLTETRAHYDROISOQUINOLINES, PROCESS FOR THEIR PREPARATION, PHARMACEUTICAL COMPOSITIONS AND THERAPEUTIC USE

(75) Inventor: Hans-Jochen Lang, Hofheim (DE)

(73) Assignee: Sanofi, Paris (FR)

( * ) Notice: Subject to any disclaimer, the term of this patent is extended or adjusted under 35 U.S.C. 154(b) by 1189 days.

(21) Appl. No.: 12/046,928

(22) Filed: Mar. 12, 2008

(65) Prior Publication Data

US 2008/0194621 A1 Aug. 14, 2008

Related U.S. Application Data

(63) Continuation of application No. PCT/EP2006/008770, filed on Sep. 8, 2006.

(30) Foreign Application Priority Data

Sep. 20, 2005 (DE) .......... 10 2005 044 817

(51) Int. Cl.
C07D 217/04 (2006.01)
A61K 31/472 (2006.01)

(52) U.S. Cl.
USPC .......... 514/307; 546/144

(58) Field of Classification Search
None
See application file for complete search history.

(56) References Cited

FOREIGN PATENT DOCUMENTS

| DE | 10312963 | 10/2004 |
|---|---|---|
| DE | 102004046492 A1 | 7/2011 |
| WO | WO 01/79186 | 10/2001 |
| WO | WO 03/048129 | 6/2003 |
| WO | WO 03/055880 | 7/2003 |
| WO | 2006/032372 | 3/2006 |

*Primary Examiner* — Zinna Northington Davis
(74) *Attorney, Agent, or Firm* — Scully, Scott, Murphy & Presser, P.C.

(57) ABSTRACT

The present invention relates to substituted 4-phenyltetrahydroisoquinoline compounds and pharmaceutical compositions comprising them which are excellent inhibitors of the sodium-hydrogen exchanger (NHE), in particular of the sodium-hydrogen exchanger of subtype 3 (NHE-3). As such these compounds are useful in the treatment of various disorders of the renal and respiratory systems such as acute or chronic renal failure, pulmonary complications, biliary function disorders, respiratory disorders such as snoring or sleep apneas and cardiovascular/central nervous system disorders such as stroke. More specifically, the present invention relates to substituted 4-phenyl-tetrahydroisoquinolines defined by the formula I

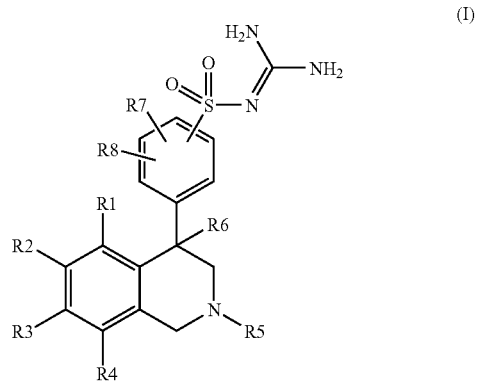

in which R1-R8 are defined herein.

15 Claims, No Drawings

SUBSTITUTED 4-PHENYLTETRAHYDROISOQUINOLINES, PROCESS FOR THEIR PREPARATION, PHARMACEUTICAL COMPOSITIONS AND THERAPEUTIC USE

CROSS-REFERENCE TO RELATED APPLICATIONS

This application is a continuation of International Patent Application No. PCT/EP2006/008770 filed on Sep. 8, 2006 which is incorporated herein by reference in its entirety which also claims the benefit of priority of German Patent Application No. 10 2005 044 817.8 filed on Sep. 20, 2005.

FIELD OF THE INVENTION

The present invention relates generally to pharmaceutical compositions for the treatment of renal disorders and the diseases and the physiological manifestations resulting therefrom. More specifically, the present invention relates to substituted 4-phenyltetrahydroisoquinolines their derivatives and their salts which are able to therapeutically renal disorders such as acute or chronic kidney failure, disorders of biliary function and other renal disorders that may result in the event of respiratory disorders such as snoring or sleep apneas.

BACKGROUND OF THE INVENTION

Compounds and pharmaceutical compositions of the present invention of this type are useful in the prevention or treatment of various disorders. For instance, the substituted 4-phenyltetrahydroisoquinoline compounds and pharmaceutical compositions comprising them which are excellent inhibitors of the sodium-hydrogen exchanger (NHE) are of surprising therapeutic value in the treatment of acute and chronic disorders of the kidneys and of the intestines, disorders resulting from ischemic and/or reperfusion events, as well as those resulting from proliferative or fibrotic events, The NHE inhibitors known in the prior art are derived, for example, from acylguanidine-type compounds (EP825178), norbornylamine-type compounds (WO0144164), 2-guanidinoquinazoline type compounds (WO0179186), benzamidine type compounds (WO0121582, WO0172742) or tetrahydroisoquinoline type-compounds (WO03048129, WO03055880). Squalamine, which has likewise been described as an NHE inhibitor (M. Donowitz et al. Am. J. Physiol. 276 (Cell Physiol. 45): C136-C144), similar to that of the acylguanidine- and norbornylamine-type compounds, does not act directly upon administration but rather via an indirect mechanism and thus does not achieve its maximum strength of action until after one hour. Since these types of NHE inhibitors have different types of mechanistic action, they are suitable, for example, in combination with those compounds of the present invention.

Clonidine, which is distantly related to the inventive compounds, is known to be a weak NHE inhibitor. However, its action on the NHE of the rat is extremely moderate at a half-maximum inhibitory concentration ($IC_{50}$) of 620 µM. Instead, it has a certain selectivity for the NHE (J. Orlowski et al. J. Biol. Chem. 268, 25536). It should therefore be referred to rather as an NHE inhibitor. In addition to the weak NHE action, clonidine has a high affinity for the adrenergic alpha-2 receptor and the imidazoline receptor, which results in a strong blood sugar-lowering action (Ernsberger et al. Eur. J. Pharmacol. 134, 1, 1987).

Compounds which are similar to clonidine but have a thiophene instead of the phenyl ring are disclosed in DE1941761. The structures of formula I disclosed and claimed herein differ from existing compounds by the fusing of a thieno-substituent to the imidazole moiety of the formula I or II. This distinction allows the above-described clonidine-like undesired cardiovascular effects mediated by alpha-adrenoreceptor action to be eliminated. At the same time, as a consequence of the substitution differences, the NHE-inhibiting properties of the compounds described here are enhanced down to the micromolar and submicromolar range, while the compounds disclosed by DE1941761 exhibit only very weakly pronounced NHE-inhibiting effects, if any. For instance, the hypotensive compound described in the application DE1941761, tiamenidine, in a therapeutically utilizable concentration range, has no relevant inhibitory actions on any of the NHE subtypes investigated, NHE-1, NHE-2, NHE and NHE-5. The application WO03053434 proposes NHE inhibitors of the imidazoline type, the patent application WO 03101984 of the thiophene type and the application DE10304374 of the imidazole type.

Tetrahydroisoquinolines have been previously described as inhibitors of the sodium-hydrogen exchanger of subtype 3 (NHE-3) see WO03048129 and DE10312963. WO03055880 describes a related class of tetrahydroisoquinolinium salt compounds as NHE inhibitors. It has now been surprisingly found that the compounds of formula I described herein are also potent inhibitors of NHE and have beneficial pharmacological and pharmacokinetic properties. Thus, the compounds are notable for improved properties such as a high selectivity for the sodium-hydrogen exchanger with a negligible effect on hERG potassium channels. NHE is found in the body of various species preferentially in the bile, the intestine and the kidney (Larry Fliegel et al., Biochem. Cell. Biol. 76: 735-741, 1998), but has also been detected in the brain (E. Ma et al., Neuroscience 79:591-603).

On the basis of the NHE-inhibitory properties, the substituted 4-phenyl-tetrahydroisoquinoline compounds of the present invention as defined as the structure of formula I herein and their pharmaceutically acceptable salts are suitable for the prevention and treatment of diseases caused by the activation of or by an activated NHE. They are also useful in the treatment of diseases which are caused secondarily by the NHE-related damage.

Optionally, the NHE inhibitors described herein can be combined with other compounds which also regulate the intracellular pH environment Suitable combination comprise the formulation with other inhibitors of the enzyme group of carbonic anhydrases and inhibitors of the transport systems that carry bicarbonate ions, such as of the sodium-bicarbonate co-transporter (NBC) or of the sodium-dependent chloride-bicarbonate exchanger, and with other NHE inhibitors with an inhibitory effect on other NHE subtypes, because the pharmacologically relevant pH-regulating effects of the NHE inhibitors described herein can be enhanced or modulated thereby.

The use of compounds of the present invention relates to the prevention and the treatment of acute and chronic diseases in veterinary and human medicine.

The pharmacological effect of the compounds of the formula I is characterized in that they lead to an improvement in the respiratory drive. They can therefore be used for the treatment of impaired respiratory mechanisms and therefore useful in the treatment of acute and chronic disorders of the kidneys, intestines, as well as disorders resulting from ischemic and/or reperfusion events, as well as those resulting from proliferative or fibrotic events, In the present invention, it has surprisingly been possible to show that the compounds of formula I, below, constitute potent inhibitors of sodium/proton exchange (NHE), especially of sub-type 3 sodium/proton exchanger (NHE).

SUMMARY OF THE INVENTION

The present invention relates to substituted 4-phenyltetrahydroisoquinoline compounds and pharmaceutical compositions comprising them which are excellent inhibitors of the sodium-hydrogen exchanger (NHE), in particular of the sodium-hydrogen exchanger of subtype 3 (NHE-3). As such these compounds are useful in the treatment of various disorders of the renal and respiratory systems such as acute or chronic renal failure, pulmonary complications, biliary function disorders, respiratory disorders such as snoring or sleep apneas and cardiovascular/central nervous system disorders such as stroke. More specifically, the present invention relates to substituted 4-phenyl-tetrahydroisoquinolines defined by the formula I

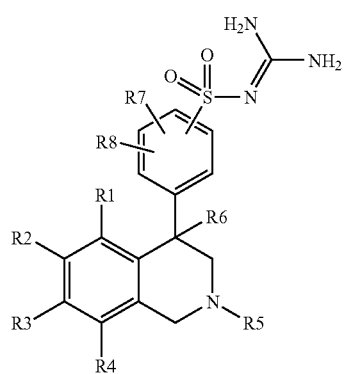

in which:
R1-R8 are defined herein
and derivatives thereof as well as compositions comprising them which may be optionally formulated in combination with other compounds which also regulate the intracellular pH environment such as inhibitors of carbonic anhydrase and inhibitors of the transport systems that carry bicarbonate ions, such as of the sodium-bicarbonate co-transporter (NBC) or the sodium-dependent chloride-bicarbonate exchanger

DETAILED DESCRIPTION OF THE INVENTION

The invention relates to substituted 4-phenyltetrahydroisoquinolines compounds of formula I which are useful in the prevention or treatment of various disorders such as renal disorders comprising acute or chronic kidney failure, other disorders and manifestations of biliary function as well as respiratory disorders such as snoring or sleep apneas. These compounds are defined by formula I

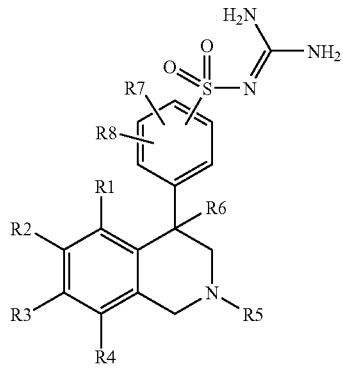

in which:
R1, R2, R3 and R4 are each independently selected from the group consisting of hydrogen, F, Cl, Br, I, CN, $NO_2$ or R11-$(C_mH_{2m})$-$A_n$-;
m is zero, 1, 2, 3 or 4;
n is zero or 1;
R11 is hydrogen, methyl or $C_pF_{2p+1}$;
A is oxygen, NH, $N(CH_3)$ or $S(O)_q$;
p is 1, 2 or 3;
q is zero, 1 or 2;
R5 is selected from the group consisting of hydrogen, alkyl having 1, 2, 3, 4, 5 or 6 carbon atoms or cycloalkyl having 3, 4, 5 or 6 carbon atoms;
R6 is selected from the group consisting of hydrogen, OH, F, $CF_3$, alkyl having 1, 2, 3 or 4 carbon atoms or cycloalkyl having 3, 4, 5 or 6 carbon atoms;
R7 and R8 are each independently selected from the group consisting of hydrogen, F, Cl, Br, CN, $CO_2R12$, NR13R14 and R16-$(C_{mm}H_{2mm})$-$E_{nn}$-;
R12 is hydrogen selected from the group consisting of, alkyl having 1, 2, 3 or 4 carbon atoms or cycloalkyl having 3, 4, 5 or 6 carbon atoms;
R13 and R14 are each independently selected from the group consisting of hydrogen, alkyl having 1, 2, 3 or 4 carbon atoms or cycloalkyl having 3, 4, 5 or 6 carbon atoms; or
R13 and R14, including the nitrogen atom to which they are bonded, form a 4-, 5-, 6- or 7-membered ring in which one $CH_2$ group may be replaced by NR15, S or oxygen;
R15 is hydrogen, alkyl having 1, 2, 3 or 4 carbon atoms or cycloalkyl having 3, 4, 5 or 6 carbon atoms;
mm is zero, 1, 2, 3 or 4;
nn is zero or 1;
R16 is hydrogen, methyl or $C_{pp}F_{2pp+1}$;
E is oxygen or $S(O)_{qq}$;
pp is 1, 2 or 3;
qq is zero, 1 or 2;
and also their pharmaceutically acceptable salts and trifluoroacetates.

In one embodiment, preference is given to compounds of the formula I in which
R1, R2, R3 and R4 are each independently selected from the group consisting of hydrogen, F, Cl, Br, CN or R11-$(C_mH_{2m})$-$A_n$-;
m is zero or 1;
n is zero or 1;
R11 is hydrogen, methyl or $C_pF_{2p+1}$;

A is oxygen, NCH$_3$ or S(O)$_q$;
  p is 1 or 2;
  q is zero, 1 or 2;
R5 is selected from the group consisting of hydrogen, methyl, ethyl or cyclopropyl;
R6 is hydrogen or methyl;
R7 and R8 are each independently selected from the group consisting of hydrogen, F, Cl, CN, CO$_2$R12, NR13R14 and R16-(C$_{mm}$H$_{2mm}$)-E$_{nn}$-;
R12 is hydrogen, methyl or ethyl;
R13 and R14 are each independently hydrogen, alkyl having 1, 2, 3 or 4 carbon atoms or cycloalkyl having 3, 4, 5 or 6 carbon atoms;
  or
R13 and R14, together with the nitrogen atom to which they are bonded, form a 5-, 6- or 7-membered ring in which one CH$_2$ group may be replaced by NR15, S or oxygen;
R15 is hydrogen, alkyl having 1, 2, 3 or 4 carbon atoms or cycloalkyl having 3, 4, 5 or 6 carbon atoms;
  mm is zero, 1 or 2;
  nn is zero or 1;
  R16 is hydrogen, methyl or C$_{pp}$F$_{2pp+1}$;
  E is oxygen or S(O)$_{qq}$;
    pp is 1 or 2;
    qq is zero, 1 or 2;
and also their pharmaceutically acceptable salts and trifluoroacetates.

Preferably, compounds of formula I are those in which
R1 and R3 are each hydrogen;
R2 and R4 are each independently selected from the group consisting of hydrogen, F, Cl, NH$_2$, NHCH$_3$ or N(CH$_3$)$_2$;
R5 is hydrogen, methyl, ethyl or cyclopropyl;
R6 is hydrogen or methyl;
R7 and R8 are each hydrogen;
and also their pharmaceutically acceptable salts and trifluoroacetates.

Most preferably, formula I is N-diaminomethylene-4-(6,8-dichloro-2-methyl-1,2,3,4-tetrahydroisoquinolin-4-yl)benzenesulfonamide and also its pharmaceutically acceptable salts and trifluoroacetates.

In one embodiment, preferred compounds are those of formula I in which the R1, R2, R3 and R4 substituents are each independently selected from the group consisting of hydrogen, F, Cl, Br, CN or R11-(C$_m$H$_{2m}$)-A$_n$- where m and n are each independently zero or 1, R11 is hydrogen, methyl or C$_p$F$_{2p+1}$ and A is oxygen, NCH$_3$ or S(O)$_q$, where p is 1 or 2 and q is zero, 1 or 2; more preferably, compounds of formula I comprise those in which R1 and R3 are each hydrogen and R2 and R4 are each independently hydrogen, F, Cl, NH$_2$, NHCH$_3$ or N(CH$_3$)$_2$, for example Cl. In one embodiment, preference is given to compounds of the formula I in which R2 and R4 are not hydrogen.

In another embodiment, preference is given to compounds of formula I in which R5 is hydrogen, methyl, ethyl or cyclopropyl, In yet a further embodiment, preference is given to compounds of the formula I in which R6 is described by hydrogen or methyl.

In another embodiment, preference is given to compounds of the formula I in which the R7 and R8 radicals are each independently described by hydrogen, F, Cl, CN, CO$_2$R12, NR13R14 or R16-(C$_{mm}$H$_{2mm}$)-E$_{nn}$-, where R12 is hydrogen, methyl or ethyl, R13 and R14 are each independently selected from the group consisting of hydrogen, alkyl having 1, 2, 3 or 4 carbon atoms or cycloalkyl having 3, 4, 5 or 6 carbon atoms, or R13 and R14, together with the nitrogen atom to which they are bonded, form a 5-, 6- or 7-membered ring in which one CH$_2$ group may be replaced by NR15, S or oxygen, and where R15 is hydrogen, alkyl having 1, 2, 3 or 4 carbon atoms or cycloalkyl having 3, 4, 5 or 6 carbon atoms, and where mm is zero, 1 or 2, nn is zero or 1, and R16 is hydrogen, methyl or C$_{pp}$F$_{2pp+1}$, where E is oxygen or S(O)$_{qq}$, where pp is 1 or 2 and qq is zero, 1 or 2; particular preference is given to compounds of formula I in which R7 and R8 are each hydrogen.

When the compounds of the formula I contain one or more centers of asymmetry, they may each independently have either S or R configuration. The compounds may be present as optical isomers, as diastereomers, as racemates or as mixtures in all ratios thereof.

The present invention encompasses all possible tautomeric forms of the compounds of the formula I.

The present invention also encompasses derivatives of the compounds of the formula I, for example solvates such as hydrates and alcohol adducts, esters, prodrugs and other physiologically acceptable derivatives of the compounds of the formula I, and also active metabolites of the compounds of the formula I. The invention likewise encompasses all crystal modifications of the compounds of the formula I.

Alkyl radicals may be straight-chain or branched. This is also true when they bear substituents or occur as substituents of other radicals, for example in fluoroalkyl radicals or alkoxy radicals. Examples of alkyl radicals are methyl, ethyl, n-propyl, isopropyl (=1-methylethyl), n-butyl, isobutyl (=2-methylpropyl), sec-butyl (=1-methylpropyl), tert-butyl (=1,1-dimethylethyl), n-pentyl, isopentyl, tert-pentyl, neopentyl and hexyl. Preferred alkyl radicals are methyl, ethyl, n-propyl, isopropyl and n-butyl. In alkyl radicals, one or more, for example 1, 2, 3, 4, 5, 6, 7, 8, 9, 10, 11, 12, 13 or 14, hydrogen atoms may be substituted by fluorine atoms. Examples of such fluoroalkyl radicals are trifluoromethyl, 2,2,2-trifluoroethyl, pentafluoroethyl, heptafluoroisopropyl. Substituted alkyl radicals may be substituted in any positions.

Alkylene radicals, for example C$_m$H$_{2m}$, C$_{mm}$H$_{2mm}$ or C$_r$H$_{2r}$, may be straight-chain or branched. This is also true when they bear substituents or occur as substituents of other radicals, for example in fluoroalkylene radicals, for example in C$_p$F$_{2p}$ and C$_{pp}$F$_{2pp}$. Examples of alkylene radicals are methylene, ethylene, 1-methylmethylene, propylene, 1-methylethylene, butylene, 1-propylmethylene, 1-ethyl-1-methylmethylene, 1,2-dimethylethylene, 1,1-dimethylmethylene, 1-ethylethylene, 1-methylpropylene, 2-methylpropylene, pentylene, 1-butylmethylene, 1-propylethylene, 1-methyl-2-ethylethylene, 1,2-dimethylpropylene, 1,3-dimethylpropylene, 2,2-dimethyl propylene, hexylene and 1-methylpentylene. In alkylene radicals, one or more, for example 1, 2, 3, 4, 5, 6, 7, 8, 9, 10, 11 or 12, hydrogen atoms may be substituted by fluorine atoms. Substituted alkylene radicals may be substituted in any positions. In the alkylene radicals, one or more CH$_2$ groups may be replaced by oxygen, S, NH, N-alkyl or N-cycloalkyl.

Examples of cycloalkyl radicals are cyclopropyl, cyclobutyl, cyclopentyl or cyclohexyl. In cycloalkyl radicals, one or more, for example 1, 2, 3, 4, 5, 6, 7, 8, 9, 10, 11 or 12, hydrogen atoms may be substituted by fluorine atoms. Substituted cycloalkyl radicals may be substituted in any positions. Cycloalkyl radicals may also be present in branched form as alkylcycloalkyl or cycloalkylalkyl, for example methylcyclohexyl or cyclohexylmethyl.

Examples of rings from NR13R14 where R13 and R14 with the nitrogen atom to which they are bonded form a 4-, 5-, 6- or 7-membered ring, in which one CH$_2$ group may be replaced by NR15, sulfur or oxygen, are morpholine, pyrrolidine, piperidine, piperazine and N-methylpiperazine.

When a variable occurs more than once as a component, the definitions of the variables are independent from one another in each instance.

When the compounds of the formula I contain one or more acidic or basic groups or one or more basic heterocycles, the corresponding physiologically or toxicologically acceptable salts are also included in the invention, especially the pharmaceutically usable salts. For instance, the compounds of the formula I can be deprotonated at an acidic group and be used, for example, in the form of alkali metal salts, preferably sodium or potassium salts, or in the form of ammonium salts, for example as salts with ammonia or organic amines or amino acids. Since compounds of the formula I always contain at least one basic group, they may also be prepared in the form of their physiologically acceptable acid addition salts, for example with the following acids: from inorganic acids such as hydrochloric acid, sulfuric acid or phosphonic acid, or from organic acids such as acetic acid, citric acid, tartaric acid, lactic acid, malonic acid, methanesulfonic acid, fumaric acid. Useful acid addition salts include salts of all pharmacologically acceptable salts, for example halides, especially hydrochlorides, lactates, sulfates, citrates, tartrates, acetates, phosphates, methylsulfonates, p-toluenesulfonates, adipates, fumarates, gluconates, glutamates, glycerolphosphates, maleates and pamoates (this group also corresponds to the physiologically acceptable anions); but also trifluoroacetates.

The invention also provides the processes described below for the preparation of the compounds of formula I.

The compounds of the formula I described here can be prepared by chlorosulfonating compounds of the formula VIII by means of processes known to those skilled in the art with subsequent reaction with guanidine by processes known to those skilled in the art (as described, for example, in Synthetic Communications, 33(7), 1073; 2003).

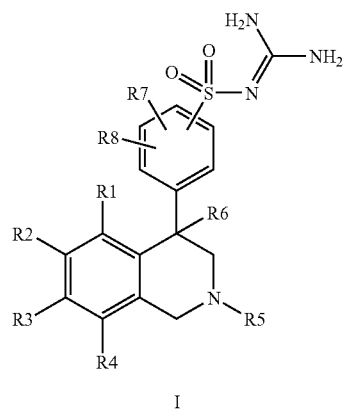

I

There is no need to isolate the intermediate of the formula XII obtained after the chlorosulfonation, and it may instead be reacted further directly with guanidine.

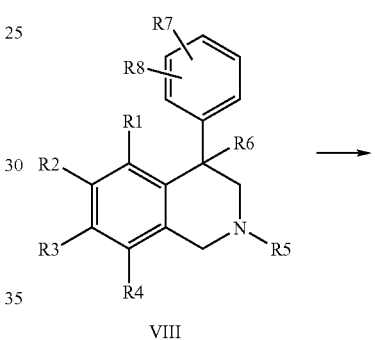

VIII

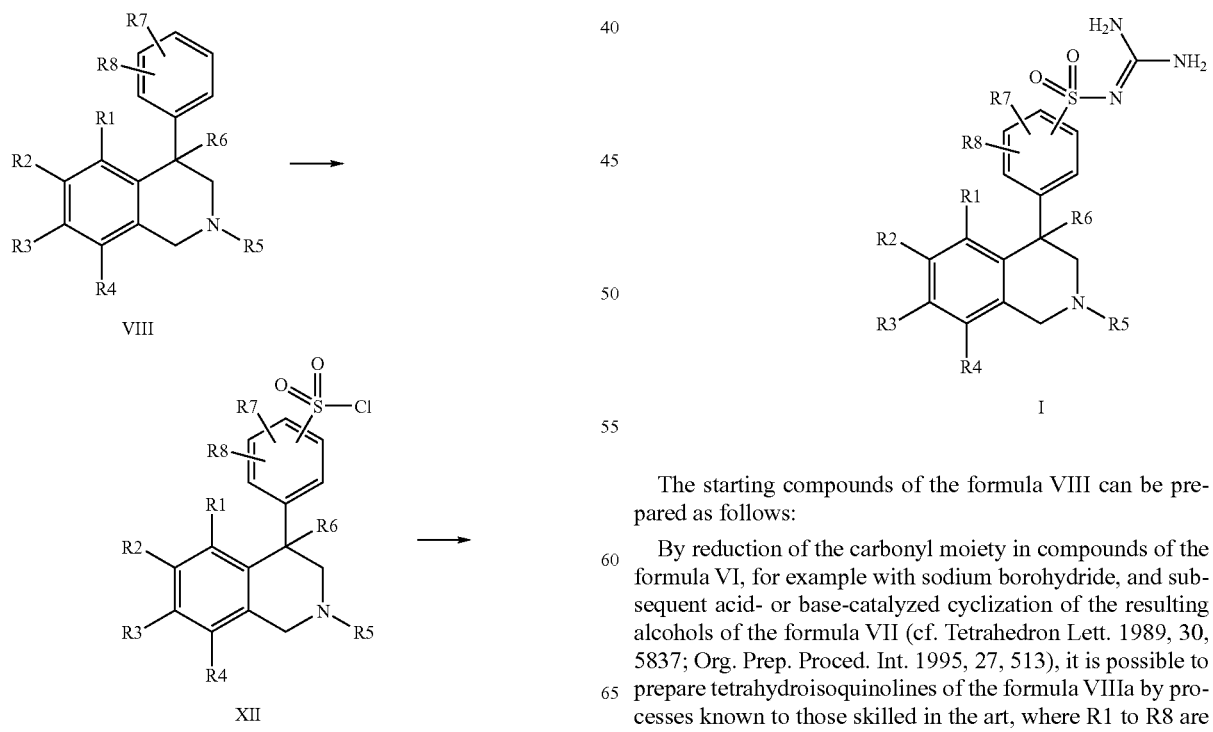

The starting compounds of the formula VIII can be prepared as follows:

By reduction of the carbonyl moiety in compounds of the formula VI, for example with sodium borohydride, and subsequent acid- or base-catalyzed cyclization of the resulting alcohols of the formula VII (cf. Tetrahedron Lett. 1989, 30, 5837; Org. Prep. Proced. Int. 1995, 27, 513), it is possible to prepare tetrahydroisoquinolines of the formula VIIIa by processes known to those skilled in the art, where R1 to R8 are each as defined above.

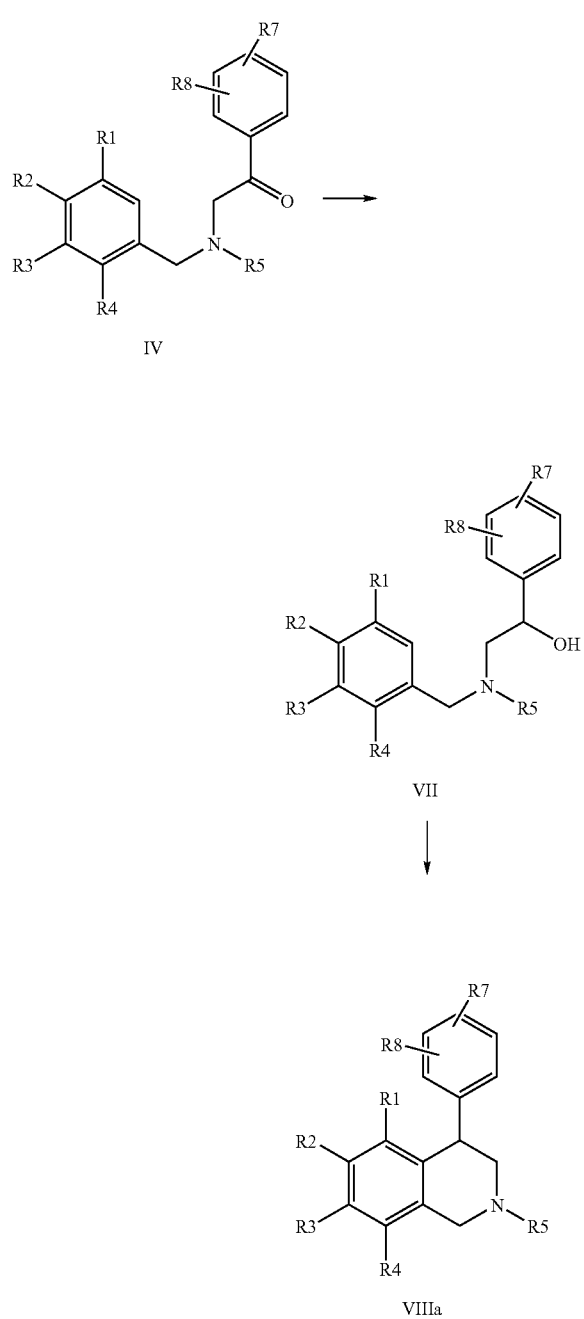

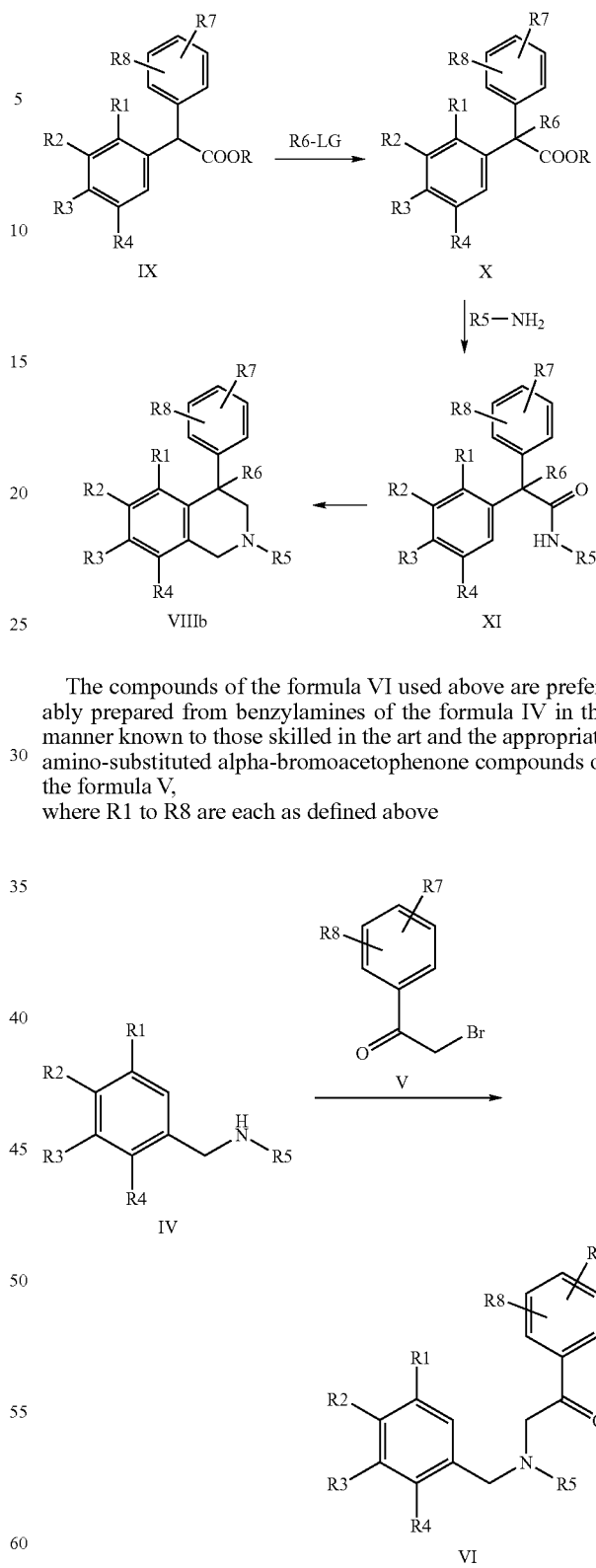

The compounds of the formula VI used above are preferably prepared from benzylamines of the formula IV in the manner known to those skilled in the art and the appropriate amino-substituted alpha-bromoacetophenone compounds of the formula V,
where R1 to R8 are each as defined above The alpha-bromoacetophenone compounds of the formula V can be obtained in literature processes from the corresponding acetophenone precursors by bromination.

If commercially unavailable, the benzylamine precursors of the formula IV can be synthesized by standard processes To prepare alkyl-branched compounds of the formula I in which R6 is not hydrogen, the corresponding diphenylacetic esters of the formula IX can be alkylated in the alpha position with R6 by known methods. The compounds of the formula X can be converted by standard processes to the corresponding amides of the formula XI which are converted in a Pictet-Spengler-like reaction to the desired tetrahydroisoquinolines of the formula VIIIb (cf. Tetrahedron 1987, 43, 439; Chem. Pharm. Bull. 1985, 33, 340), where R1 to R8 are each as defined above, and LG corresponds to a leaving group common in alkylations, for example chloride, bromide, tosylate or mesylate.

known to those skilled in the art from the corresponding benzyl halides, for example benzyl chlorides or bromides, of the formula III and the corresponding amines R5-NH$_2$, where R1 to R5 are each as defined above and X is F, Cl, Br or I, in particular Cl or Br.

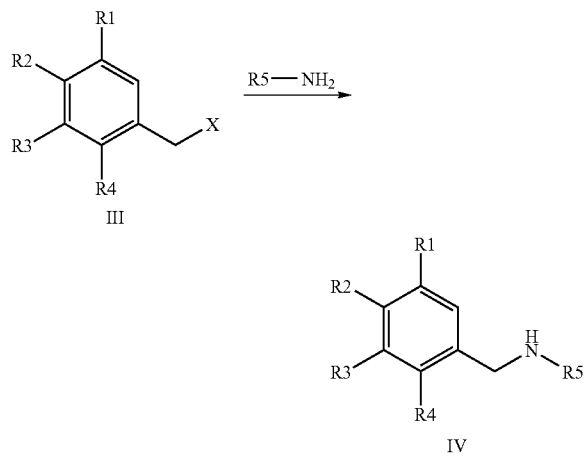

Alternatively, compounds of the formula IV are also obtainable by reductive amination of an aldehyde of the formula IIIa by standard processes known to those skilled in the art,
where R1 to R5 are each as defined above.

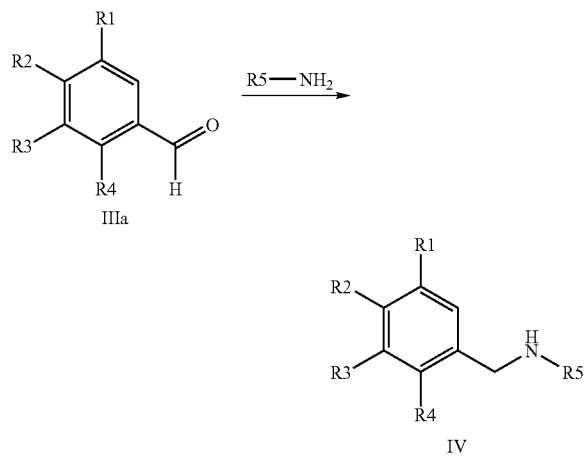

The compounds of the formulae III and IIIa, IX and R6-LG and R5-NH$_2$ are commercially available or can be prepared according to or analogously to processes which are described in the literature and are known to those skilled in the art.

The products and/or intermediates are worked up and, if desired, purified by the customary methods such as extraction, chromatography or crystallization and the customary drying steps.

It has been possible to show that compounds of the formula I are outstanding inhibitors of the sodium-hydrogen exchanger (NHE), especially the sodium-hydrogen exchanger of the subtype 3 (NHE). In addition, the compounds of the formula I are also outstanding inhibitors of the sodium-hydrogen exchanger of the subtype 5 (NHE5).

As a consequence of their pharmacological actions, the compounds of the formula I are especially suitable for improving the respiratory drive. They can therefore be employed for the treatment of disturbed respiratory states, as can occur, for example, in the event of the following clinical states and disorders: disturbed central respiratory drive (for example central sleep apneas, sudden infant death, postoperative hypoxia), muscular-related respiratory disorders, respiratory disorders after long-term ventilation, respiratory disorders in the course of adaptation in high mountains, obstructive and mixed forms of sleep apneas, acute and chronic pulmonary disorders with hypoxia and hypercapnea.

In addition, the compounds increase the muscle tone of the upper airways, so that snoring is suppressed. The compounds mentioned therefore advantageously find use for the preparation of a medicament for the prevention and treatment of sleep apneas and muscular-related respiratory disorders, and for the preparation of a medicament for the prevention and treatment of snoring.

A combination of an NHE inhibitor of the formula I with a carbonic anhydrase inhibitor (for example acetazolamide) can be found to be advantageous, the latter bringing about metabolic acidosis and thus itself increasing respiratory activity, so that enhanced action and reduced use of active ingredients can be achieved.

As a consequence of their NHE-inhibitory action, the inventive compounds protect the cellular energy reserves which are rapidly depleted in toxic and pathogenic events and thus lead to cell damage or to cell death. The energy-intensive ATP-consuming sodium absorption in the proximal tubulus is temporarily shut down under the influence of NHE inhibitors and the cell can thus survive an acute pathogenic, ischemic or toxic situation. The compounds are therefore suitable, for example, as medicaments for the treatment of ischemic noxae, for example of acute renal failure. Moreover, the compounds are also suitable for the treatment of all chronic renal disorders and nephritis forms which lead to chronic kidney failure as a consequence of increased protein deposition. Accordingly, the compounds of the formula I are suitable for preparing a medicament for the treatment of late diabetic damage, diabetic nephropathy and chronic renal disorders, especially of all renal inflammations (nephritides) which are associated with increased protein/albumin deposition.

It has been found that the compounds used in accordance with the invention have a mild laxative effect and can accordingly also be used advantageously as laxatives or in the event of impending constipation.

Moreover, the inventive compounds may be used advantageously for the prevention and therapy of acute and chronic disorders of the intestinal tract which are induced, for example, by ischemic states in the intestinal region and/or by subsequent reperfusion or by inflammatory states and events. Such complications may occur, for example, as a result of inadequate bowel peristalsis, as are observed, for example, frequently after surgical interventions, in the event of constipation or greatly reduced bowel activity.

The compounds of the present invention may also be used in the prevention of gallstone formation.

The inventive NHE inhibitors are suitable generally for the treatment of disorders which are caused by ischemia and by reperfusion.

The compounds of the present invention are also suitable as antiarrhythmic pharmaceuticals. Moreover, as a result of their cardioprotective component, the NHE inhibitors are outstandingly suitable for infarction prophylaxis and infarction treatment, and also for the treatment of angina pectoris, in which cases they also inhibit or greatly reduce the pathophysiological processes in the development of ischemically induced states, especially in the triggering of ischemically induced cardiac arrhythmias. Owing to their protective actions against pathological hypoxic and ischemic situations, the compounds of the formula I used in accordance with the invention, as a consequence of inhibition of the cellular $Na^+/H^+$ exchange mechanism, may be used as pharmaceuticals for the treatment of all acute or chronic damage induced by ischemia or diseases induced primarily or secondarily thereby.

The pharmaceutical compounds of the present invention are also useful in surgical interventions. For instance, the inventive compounds may be used in organ transplants, in which case the compounds may be used both for the protection of the organs in the donor before and during the removal, for the protection of removed organs, for example in the course of treatment with or their storage in physiological bath liquids, and also in the course of transfer into the recipient organism pretreated with compounds of the formula I.

The compounds are likewise valuable, protective medicaments in the performance of angioplastic surgical interventions, for example on the heart, and also on peripheral organs and vessels.

Moreover, the inventive compounds may be used in the performance of bypass operations, for example in bypass operations on coronary vessels and in coronary artery bypass graft (CABG).

In accordance with their action against ischemically induced damage, the inventive compounds of the formula I may also be used in resuscitation after a cardiac arrest.

In accordance with their protective action against ischemically induced damage, the compounds are also suitable as medicaments for the treatment of ischemias of the nervous system, especially of the CNS, in which case they are suitable, for example, for the treatment of stroke or of cerebral edema.

Since NHE inhibitors protect human tissue and organs effectively not only against damage which is caused by ischemia and reperfusion but also against the cytotoxic action of medicaments as find use especially in cancer therapy and the therapy of autoimmune disorders, their combined administration with compounds of the formula I is suitable for reducing or for suppressing the cytotoxic effects of a therapy. The reduction in the cytotoxic effects, especially in the cardiotoxicity, as a consequence of co-medication with NHE inhibitors also allows the dose of the cytotoxic therapeutic agents to be increased and/or the medication with such medicaments to be prolonged. The therapeutic benefit of such a cytotoxic therapy can be considerably enhanced by the combination with NHE inhibitors. The compounds of the formula I are suitable in particular for improving the therapy with medicaments which have an undesired cardiotoxic component.

Generally, the NHE inhibitors described here can be combined favorably with other compounds which likewise regulate the intracellular pH, in which case possible combination partners are inhibitors of the enzyme group of the carbonic anhydrases, inhibitors of the systems transporting bicarbonate ions, such as the sodium bicarbonate cotransporter (NBC) or the sodium-dependent chloride-bicarbonate exchanger (NCBE), and also with other NHE inhibitors with inhibitory action on other NHE subtypes, because they can enhance or modulate the pharmacologically relevant pH-regulating effects of the NHE inhibitors described here.

In accordance with their protective action against ischemically induced damage, the inventive compounds are also suitable as medicaments for the treatment of ischemias of the nervous system, especially of the central nervous system, in which case they are suitable, for example, for the treatment of stroke or of cerebral edema.

The compounds of the formula I are also suitable for the therapy and prophylaxis of diseases and disorders which are induced by overexcitability of the central nervous system, especially for the treatment of epileptic disorders, centrally induced clonic and tonic spasms, states of psychological depression, anxiety disorders and psychoses. In these cases, the inventive NHE inhibitors may be employed alone or in combination with other antiepileptically active substances or antipsychotic active substances, or carbonic anhydrase inhibitors, for example with acetazolamide, and also with further inhibitors of the NHE or of the sodium-dependent chloride-bicarbonate exchanger (NCBE).

Furthermore, the inventive compounds of the formula I are likewise suitable for the treatment of types of shock, for example of allergic, cardiogenic, hypovolemic and bacterial shock.

The compounds of the formula I may likewise be used for the prevention and for the treatment of thrombotic disorders since they, as NHE inhibitors, can also inhibit platelet aggregation themselves. They can also inhibit or prevent the excessive release, taking place after ischemia and reperfusion, of inflammation and coagulation mediators, especially of von Willebrand factor and of thrombogenic selectin proteins. This allows the pathogenic action of thrombogenic and inflammation-relevant factors to be reduced and eliminated. Therefore, it is possible to combine the NHE inhibitors of the present invention with further anticoagulative and/or thrombolytic active ingredients, for example recombinant or natural tissue plasminogen activator, streptokinase, urokinase, acetylsalicylic acid, thrombin antagonists, factor Xa antagonists, fibrinolytically active medicaments, thromboxane receptor antagonists, phosphodiesterase inhibitors, factor VIIa antagonists, clopidogrel, ticlopidin, etc. Combined use of the present NHE inhibitors with NCBE inhibitors and/or with inhibitors of carbonic anhydrase, for example with acetazolamide, is particularly favorable.

Furthermore, the inventive NHE inhibitors feature strong inhibiting action on the proliferations of cells, for example fibroblast cell proliferation and the proliferation of smooth vascular muscle cells. The compounds of the formula I are therefore useful as valuable therapeutic agents for disorders in which cell proliferation constitutes a primary or secondary cause, and can therefore be used as antiatherosclerotics, agents against chronic renal failure, cancers. They may thus be used for the treatment of organ hypertrophies and hyperplasias, for example of the heart and of the prostate. Compounds of the formula I are therefore suitable for the prevention and for the treatment of heart failure (congestive heart failure=CHF) and also in the treatment and prevention of prostate hyperplasia or prostate hypertrophy.

NHE inhibitors also feature a retardation or prevention of fibrotic disorders. They are thus suitable as outstanding agents for the treatment of fibroses of the heart, and also of pulmonary fibrosis, hepatic fibrosis, renal fibrosis and other fibrotic disorders.

Since there is significant elevation in the NHE in essential hypertensives, the compounds of the formula I are suitable for the prevention and treatment of high blood pressure and of cardiovascular disorders. In these cases, they may be used alone or with a suitable combination partner for the treatment of high blood pressure and for the treatment of cardiovascular disorders. For example, one or more diuretics with a thiazide-like action, loop diuretics, aldosterone and pseudoaldosterone antagonists, such as hydrochlorothiazide, indapamide, polythiazide, furosemide, piretanide, torasemide, bumetanide, amiloride, triamterene, spironolactone or eplerone, may be combined with compounds of the formula I. Moreover, the NHE inhibitors of the present invention may be used in combination with calcium antagonists such as verapamil, diltiazem, amlodipine or nifedipine, and with ACE inhibitors, for example ramipril, enalapril, lisinopril, fosinopril or captopril. Further favorable combination partners are also β-blockers such as metoprolol, albuterol etc., antagonists of the angiotensin receptor and its receptor subtypes such as losartan, irbesartan, valsartan, omapatrilat, gemopatrilat, endothelin antagonists, renin inhibitors, adenosine receptor agonists, inhibitors and activators of potassium channels such as glibenclamide, glimepiride, diazoxide, cromakalim, minoxidil and derivatives thereof, activators of the mitochondrial ATP-sensitive potassium channel (mitoK(ATP) channel), inhibitors of further potassium channels, such as Kv1.5, etc.

Owing to their antiinflammatory effect, inventive NHE inhibitors may be used as antiinflammatory drugs. In mechanistic terms, inhibition of the release of mediators of inflammation is notable in this connection. The compounds can thus be used alone or in combination with an antiinflammatory drug in the prevention or treatment of chronic and acute inflammatory disorders. The combination partners used are advantageously steroidal and non-steroidal antiinflammatory drugs.

It has additionally been found that NHE inhibitors show a beneficial effect on serum lipoproteins. They can therefore be used for the prophylaxis and regression of atherosclerotic lesions by eliminating a causal risk factor. These include not only the primary hyperlipidemias but also certain secondary hyperlipidemias as occur, for example, in the case of diabetes. In addition, NHE inhibitors lead to a distinct reduction in the infarctions induced by metabolic abnormalities and especially to a significant reduction in the induced infarction size and the severity thereof. NHE inhibitors of the formula I therefore advantageously find use for the preparation of a medicament for the treatment of hypercholesterolemia; for the preparation of a medicament for the prevention of atherogenesis; for the preparation of a medicament for the prevention and treatment of atherosclerosis, for the preparation of a medicament for the prevention and treatment of diseases induced by elevated cholesterol levels, for the preparation of a medicament for the prevention and treatment of diseases induced by endothelial dysfunction, for the preparation of a medicament for the prevention and treatment of atherosclerosis-induced hypertension, for the preparation of a medicament for the prevention and treatment of atherosclerosis-induced thromboses, for the preparation of a medicament for the prevention and treatment of hyper-cholesterolemia-induced and endothelial dysfunction-induced ischemic damage and post-ischemic reperfusion damage, for the preparation of a medicament for the prevention and treatment of cardiac hypertrophies and cardiomyopathies and of congestive heart failure (CHF), for the preparation of a medicament for the prevention and treatment of hypercholesterolemia-induced and endothelial dysfunction-induced coronary vasospasms and myocardial infarctions, for the preparation of a medicament for the treatment of said disorders in combinations with hypotensive substances, preferably with angiotensin converting enzyme (ACE) inhibitors and angiotensin receptor antagonists. A combination of an NHE inhibitor of the formula I with an active ingredient lowering the blood fat levels, preferably with an HMG-CoA reductase inhibitor (for example lovastatin or pravastatin), the latter bringing about a hypolipidemic effect and thus increasing the hypolipidemic properties of the NHE inhibitor of the formula I constitutes a favorable combination with enhanced effect and reduced use of active ingredients.

Thus, NHE inhibitors lead to effective protection against endothelial damage of different origins. This protection of the vessels against the syndrome of endothelial dysfunction means that NHE inhibitors are valuable medicaments for the prevention and treatment of coronary vasospasms, peripheral vascular diseases, in particular intermittent claudication, atherogenesis and atherosclerosis, left-ventricular hypertrophy and dilated cardiomyopathy and thrombotic disorders.

It has additionally been found that NHE inhibitors are suitable in the treatment of non-insulin-dependent diabetes (NIDDM), in which case, for example, the insulin resistance is restrained. In this case, it may be favorable to enhance the antidiabetic activity and quality of the effect of the compounds of the invention by combining them with a biguanide such as metformin, with an antidiabetic sulfonylurea such as glyburide, glimepiride, tolbutamide etc., with a glucosidase inhibitor, with a PPAR agonist such as rosiglitazone, pioglitazone etc., with an insulin product of different administration form, with a DB4 inhibitor, with an insulin sensitizer or with meglitinide.

In addition to the acute antidiabetic effects, NHE inhibitors counteract the development of late complications of diabetes and can therefore be used as medicaments for the prevention and treatment of late damage from diabetes, such as diabetic nephropathy, diabetic neuropathy, diabetic retinopathy, diabetic cardiomyopathy and other disorders occurring as a consequence of diabetes. They may advantageously be combined with the antidiabetic medicaments described above under NIDDM treatment. The combination with a beneficial dosage form of insulin may be particularly important in this connection.

In addition to the protective effects against acute ischemic events and the subsequent equally acutely stressing reperfusion events, NHE inhibitors also exhibit direct therapeutically utilizable effects against diseases and disorders of the entire mammalian organism which are associated with the manifestations of the chronically progressive aging process and which can also occur independently of acute ischemic states and under normal, non-ischemic conditions. These pathological, age-related manifestations induced over the long aging period, such as illness, invalidity and death, which can now be made amenable to treatment with NHE inhibitors, are diseases and disorders which are essentially caused by age-related changes in vital organs and the function thereof and become increasingly important in the aging organism.

Disorders connected with an age-related functional impairment or with age-related manifestations of wear of organs are, for example, the inadequate response and reactivity of the blood vessels to contraction and relaxation reactions. This age-related decline in the reactivity of vessels to constricting and relaxing stimuli, which are an essential process of the cardiovascular system and thus of life and health, can be significantly eliminated or reduced by NHE inhibitors. One important function and a measure of the maintenance of the reactivity of vessels is the blockade or retardation of the age-related progression in endothelial dysfunction, which can be eliminated highly significantly by NHE inhibitors. NHE inhibitors are thus outstandingly suitable for the treatment and prevention of the age-related progression in endothelial dysfunction, especially of intermittent claudication. The NHE inhibitors are thus also outstandingly suitable for the prevention and treatment of myocardial infarction, of congestive heart failure (CHF) and also for the treatment and especially for the prevention of age-related forms of cancer.

In this context, a useful combination is that with hypotensive medicaments such as with ACE inhibitors, angiotensin receptor antagonists, diuretics, $Ca^{2+}$ antagonists, etc, or with metabolism-normalizing medicaments such as cholesterol-lowering agents. The compounds of the formula I are thus suitable for the prevention of age-related tissue changes and for maintaining health and prolonging life while retaining a high quality of life.

The inventive compounds are effective inhibitors of the cellular sodium-proton antiporter (Na/H exchanger) which is elevated in numerous disorders (essential hypertension, atherosclerosis, diabetes, etc), even in those cells which are readily amenable to measurements, for example in erythrocytes, thrombocytes or leukocytes. The compounds used in accordance with the invention are therefore suitable as outstanding and simple scientific tools, for example in their use as diagnostic agents for the determination and differentiation of different forms of hypertension, but also of atherosclerosis, of diabetes and of diabetic late complications, proliferative disorders, etc.

Moreover, NHE inhibitors are suitable for the treatment of disorders (human and veterinary) induced by bacteria and by protozoa. The diseases induced by protozoa are in particular malarial disorders in humans and coccidiosis in poultry. The compounds are also suitable as agents for the control of sucking parasites in human and veterinary medicine and also in crop protection. Preference is given to the use as an agent against blood-sucking parasites in human and veterinary medicine. The compounds mentioned therefore advantageously find use alone or in combination with other medicaments or active ingredients for preparing a medicament for the treatment or prophylaxis of disorders of respiratory drive, of respiratory disorders, sleep-related respiratory disorders, sleep apneas, of snoring, of acute and chronic renal disorders, of acute kidney failure and of chronic kidney failure, of disorders of intestinal function, of high blood pressure, of essential hypertension, of disorders of the central nervous system, of disorders resulting from CNS overexcitability, epilepsy and centrally induced convulsions or of states of anxiety, depressions and psychoses, of ischemic states of the peripheral or central nervous system or of stroke, of acute and chronic damage to and disorders of peripheral organs or limbs caused by ischemic events or by reperfusion events, of atherosclerosis, of disorders of lipid metabolism, of thromboses, of disorders of biliary function, of infestation by ectoparasites, of disorders caused by endothelial dysfunction, of protozoal disorders, of malaria, for the preservation and storage of transplants for surgical procedures, for use in surgical operations and organ transplants, or for the treatment of states of shock or of diabetes and late damage from diabetes, or of diseases in which cellular proliferation constitutes a primary or secondary cause, and for maintaining health and prolonging life.

The term dementia refers to a decline in intellectual capacity. It is understood to mean in particular the decrease in memory and thinking ability. Dementia in the elderly or senile dementia refers to a progressive, acquired intellectual decline in people of advanced age which is attributable to structural and/or metabolic abnormalities in the central nervous system. Approximately 7% of the population over 65 years of age suffers from dementia of varying severity. The causes of dementia vary. Alzheimer's disease is the commonest form, accounting for up to 50%, followed by vascular dementias such as multi-infarct dementia, and combinations of these two forms. Much rarer causes are tau mutations, prion diseases, polyglutamine expansion disorders such as Huntington's chorea and spinocerebellar ataxias, and Parkinsonism. Also known in addition are secondary dementias following and/or associated with infections (e.g. with HIV), brain traumas, brain tumors or intoxications (e.g. with alcohol).

The concept of memory consolidation is based on the ability of new memories to stabilize over the course of time and thus become less sensitive to interference by new information and dysfunctions of the brain. It is possible with the aid of the prevailing cellular model of long-term potentiation (LTP) to investigate essential aspects and mechanisms of memory formation and consolidation (Neuroscientist. 9: 463-474. 2003; Brain Res Brain Res Rev. 45: 30-37, 2004; Physiol Rev. 84: 87-136, 2004).

One of the most important regions of the brain in which information is stored and processed is the hippocampus formation. It has long been known that certain patterns of electrical stimulation (tetanization) in the hippocampus lead to changes in synaptic efficiency (Bliss and Lomo, J. Physiol. 232: 331-356, 1973) which are now referred to as 'long-term potentiation' or 'LTP', and which have subsequently been confirmed in other areas of the brain in a wide variety of mammals, both in vitro and in vivo. LTP is now regarded as an important component of the neuronal mechanism underlying learning and memory. It is further known that a weak LTP correlates with short-term memory, and a strong LTP with long-term memory (J. Neurosci. 20: 7631-7639, 2000; Proc Nat'l Acad Sci USA. 97: 8116-8121, 2000).

The hippocampus plays a central role in episodic, spatial and declarative learning and memory processes, it is essential for spatial orientation and recall of spatial structures and plays an important role in the control of autonomic and vegetative functions (McEwen 1999, Stress and hippocampal plasticity, Annual Review of Neuroscience 22: 105-122). In human dementing disorders there is usually impairment of learning and memory processes in which the hippocampus is involved. Animal experiments on other mammals have shown similar results.

Thus, it was possible to show that aged mice have deficits in spatial memory and in the LTP compared with young mice, and that substances which improved the LTP simultaneously reduced the memory deficits (Bach et al. 1999, Age-related defects in spatial memory are correlated with defects in the late phase of hippocampal long-term potentiation in vitro and are attenuated by drugs that enhance the cAMP signaling pathway. Proc Nat'l Acad Sci USA. 27; 96:5280-5; Fujii & Sumikawa 2001, Acute and chronic nicotine exposure reverse age-related declines in the induction of long-term potentiation in the rat hippocampus. Brain Res. 894:347-53, Clayton et al. 2002, A hippocampal NR2B deficit can mimic age-related changes in long-term potentiation and spatial learning in the Fischer 344 rat. J. Neurosci. 22:3628-37).

It was possible to show in vivo and in vitro on transgenic animals and by administration of beta-amyloid peptides that the peptides adversely affect LTP or interfere with maintenance thereof (Ye & Qiao 1999, Suppressive action produced by beta-amyloid peptide fragment 31-35 on long-term potentiation in rat hippocampus is N-methyl-D-aspartate receptor-independent: it's offset by (−)huperzine A. Neurosci Lett. 275:187-90. Rowan et al 2003, Synaptic plasticity in animal models of early Alzheimer's disease. Philos Trans R Soc Lond B Biol Sci. 358: 821-8, Gureviciene et al. 2004, Normal induction but accelerated decay of LTP in APP+PS1 transgenic mice. Neurobiol Dis 15:188-95). It was possible to correct the impairment of the LTP and of memory functions by rolipram and cholinesterase inhibitors like those also employed in human Alzheimer's therapy (Ye & Qiao 1999, Gong et al. 2004, Persistent improvement in synaptic and cognitive functions in an Alzheimer mouse model after rolipram treatment. J Clin Invest. 114:1624-34.)

It is thus to be expected that substances which improve the LTP will also have a beneficial effect on disorders associated with cognitive impairments and dementia.

It has surprisingly been found that inhibitors of cellular NHE5 enhance LTP. A memory-improving effect of the inhibitor in dementing disorders such as Alzheimer's and Alzheimer-like forms of dementia is therefore to be expected. The use of an NHE5 inhibitor has the advantage over the active ingredients employed to date for these disorders, such as acetylcholinesterase inhibitors, that systemic effects are expected to be slight or absent, because NHE5 is expressed only in neurons and is therefore brain-specific (Am. J. Physiol. Cell. Physiol. 281: C1146-C1157, 2001).

NHE5 inhibitors are therefore suitable for the treatment of neurodegenerative disorders, memory impairments and dementing disorders such as dementia in the elderly, Alzheimer's, vascular dementias such as, for example, multi-infarct dementia, combinations of Alzheimer's and cerebrovascular disorders, tau mutations, prion diseases, polyglutamine expansion disorders such as, for example, Huntington's chorea and spinocerebellar ataxias, and Parkinsonism, and for improving memory. NHE5 inhibitors are further suitable for the treatment of secondary dementias following and/or associated with infections such as, for example, with HIV, brain traumas, brain tumors or intoxications such as, for example, with alcohol.

The invention further relates to the use of the compounds of the formula I and their pharmaceutically acceptable salts for use as a medicament.

The invention also relates to medicines for human, veterinary or phytoprotective use, comprising an effective amount of a compound of the formula I and/or of a pharmaceutically acceptable salt thereof, and also medicines for human, veterinary or phytoprotective use, comprising an effective amount of a compound of the formula I and/or of a pharmaceutically acceptable salt thereof, alone or in combination with one or more other pharmacological active ingredients or medicaments.

Medicaments which comprise a compound of the formula I or its pharmaceutically acceptable salts can be administered, for example, orally, parenterally, intramuscularly, intravenously, rectally, nasally, by inhalation, subcutaneously or by a suitable transcutaneous administration form, the preferred administration depending on the particular characteristics of the disorder. The compounds of the formula I can be used alone or together with pharmaceutical excipients, both in veterinary and in human medicine, as well as in crop protection. The medicaments comprise active ingredients of the formula I and/or their pharmaceutically acceptable salts generally in an amount of from 0.01 mg to 1 g per dosage unit.

The excipients which are suitable for the desired pharmaceutical formulation are familiar to those skilled in the art on the basis of their expert knowledge. In addition to solvents, gel formers, suppository bases, tablet excipients and other active ingredient carriers, it is possible to use, for example, antioxidants, dispersants, emulsifiers, antifoams, flavorings, preservatives, solubilizers or colorings.

For an oral administration form, the active compounds are mixed with the additives suitable for this purpose, such as carriers, stabilizers or inert diluents and converted to the suitable dosage forms, such as tablets, coated tablets, and hard gelatin capsules, aqueous, alcoholic or oily solutions by the customary methods. Examples of useful inert carriers include gum arabic, magnesia, magnesium carbonate, potassium phosphate, lactose, glucose or starch, in particular corn starch. The preparation may be either in the form of dry granules or in the form of moist granules. Examples of useful oily carriers or useful solvents are vegetable or animal oils, such as sunflower oil or cod liver oil.

For subcutaneous, percutaneous or intravenous administration, the active compounds used, if desired with the substances customary for this purpose, such as solubilizers, emulsifiers or further excipients, are converted to solution, suspension or emulsion. Examples of useful solvents are: water, physiological saline or alcohols, for example ethanol, propanol, glycerol and additionally also sugar solutions such as glucose or mannitol solutions, or else a mixture of the different solvents mentioned.

Examples of suitable pharmaceutical formulations for administration in the form of aerosols or sprays are solutions, suspensions or emulsions of the active ingredient of the formula I in a pharmaceutically acceptable solvent, in particular ethanol or water, or a mixture of such solvents. If required, the formulation may also comprise other pharmaceutical excipients such as surfactants, emulsifiers and stabilizers, and also a propellant gas. Such a preparation typically contains the active ingredient in a concentration of from about 0.1 to 10% by weight, in particular from about 0.3 to 3% by weight.

The dosage of the active ingredient of the formula I to be administered and the frequency of administration depend on the potency and duration of action of the compounds used; additionally also on the nature and severity of the disease to be treated, and also on the gender, age, weight and individual responsiveness of the mammal to be treated.

On average, the daily dose of a compound of the formula I in the case of a patient weighing about 75 kg is at least 0.001 mg/kg, preferably 0.1 mg/kg, up to at most 30 mg/kg, preferably 1 mg/kg, of body weight. In acute situations, for instance immediately after suffering apnetic states in high mountains, even higher dosages may be necessary. Especially in the case of i.v. administration, for instance in a heart attack patient in the intensive care unit, up to 300 mg/kg per day may be necessary. The daily dose can be divided into one or more, for example up to 4, individual doses.

EXPERIMENTAL DESCRIPTIONS AND EXAMPLES

List of abbreviations used:

AMPA receptor-coupled channels which can be activated by α-amino-3-hydroxy-5-methyl isoxazole-4-propionate CA 1 CA=cornu ammonis (Ammon's horn), CA region 1 in the hippocampus EA ethyl acetate EPSP excitatory post-synaptic potential ES$^+$ electron spray HEP n-heptane Conc. $NH_3$ saturated aqueous $NH_3$ solution LTP long-term potentiation LTP1 early LTP (phase of LTP)

MeOH methanol mp melting point

MS mass spectroscopy

NMDA receptor-coupled channels which can be activated by N-methyl-D-aspartate

RT room temperature

STP short-term potentiation (phase of LTP)

THF tetrahydrofuran

Example 1

N-Diaminomethylene-4-(6,8-dichloro-2-methyl-1,2,3,4-tetrahydro-isoquinolin-4-yl)benzenesulfonamide, dihydrochloride

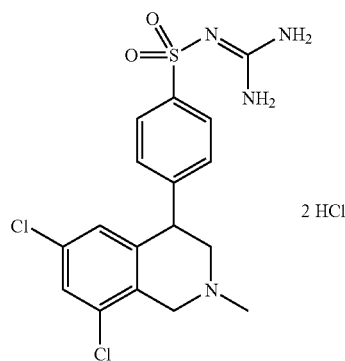 [SMILES: CN1Cc2c(Cl)cc(Cl)cc2C(c2ccc(S(=O)(=O)N=C(N)N)cc2)C1 ; "2 HCl"]

0.36 g of guanidine is suspended in 30 ml of anhydrous THF under argon, and 0.40 g of 4-(6,8-dichloro-2-methyl-1,2,3,4-tetrahydroisoquinolin-4-yl)benzenesulfonyl chloride (WO2003048129) is added. The mixture was stirred at RT for 24 h and then the THF was distilled off. 10 ml of water were added to the residue, and the precipitate was filtered off. It was washed with 10 ml of water and dried in vacuo. The solid was then suspended in 10 ml of EA, and 10 ml of a saturated solution of HCl in diethyl ether were added. The volatile constituents were removed in vacuo, and the residue was suspended in 10 ml of EA and stirred at RT for 5 h. The precipitate was then filtered off and dried in vacuo. 0.45 g was obtained, mp 140° C. (decomposition). $R_f$(EA/HEP/CH$_2$Cl$_2$/MeOH/conc. NH$_3$=10:5:5:5:1)=0.30 MS (ES$^+$):412

Pharmacological Data:

NHE and NHE5 Test Description:

In this test, the recovery in the intracellular pH (pH$_i$) of LAP1 cells, which stably express the different subtypes of the sodium-proton exchanger (NHE), after an acidification was determined. This recovery sets in even under bicarbonate-free conditions in the case of functioning NHE. To this end, the pH$_i$ was determined with the pH-sensitive fluorescent dye BCECF (Molecular Probes, Eugene, Oreg., USA; the precursor BCECF-AM is used). The cells were first incubated with BCECF (5 µM BCECF-AM) in NH$_4$Cl buffer (NH$_4$Cl buffer: 115 mM cholineCl, 20 mM NH$_4$Cl, 5 mM KCl, 1 mM CaCl$_2$, 1 mM MgCl$_2$, 20 mM Hepes, 5 mM glucose; a pH of 7.4 is established with 1 M KOH). The intracellular acidification was induced by washing the cells incubated in NH$_4$Cl buffer with NH$_4$Cl-free buffer (133.8 mM choline chloride, 4.7 mM KCl, 1.25 mM CaCl$_2$, 1.25 mM MgCl$_2$, 0.97 mM K$_2$HPO$_4$, 0.23 mM KH$_2$PO$_4$, 5 mM Hepes, 5 mM glucose; a pH of 7.4 is established with 1 M KOH). After the washing operation, 90 µl of the NH$_4$Cl-free buffer were left on the cells. The pH recovery was started by the addition of 90 µl of Na$^+$-containing buffer (133.8 mM NaCl, 4.7 mM KCl, 1.25 mM CaCl$_2$, 1.25 mM MgCl$_2$, 0.97 mM Na$_2$HPO$_4$, 0.23 mM NaH$_2$PO$_4$, 10 mM Hepes, 5 mM glucose; a pH of 7.4 is established with 1 M NaOH) in the analytical instrument (FLIPR, "Fluorometric Imaging Plate Reader", Molecular Devices, Sunnyvale, Calif., USA). The BCECF fluorescence was determined at an excitation wavelength of 498 nm and the FLIPR emission filter 1 (band gap from 510 to 570 nm). The subsequent changes in fluorescence were registered for NHE and NHE5 for two minutes as a measure of the pH recovery. For the calculation of the NHE-inhibitory potential of the tested substances, the cells were tested first in buffers in which full pH recovery, or none at all, took place. For full pH recovery (100%), the cells were incubated in Na$^+$-containing buffer (see above), and Na$^+$-free buffer for the determination of the 0% value (see above). The substances to be tested were made up in Na$^+$-containing buffer. The recovery in the intracellular pH at each tested concentration of a substance was expressed in percent of the maximum recovery. From the percentages of the pH recovery, the IC$_{50}$ value of the particular substance for the individual NHE subtypes was calculated by means of the program XLFit (idbs, Surrey, UK).

|  | NHE IC$_{50}$ [µM] | NHE5 IC$_{50}$ [µM] |
|---|---|---|
| Example 1 | 0.035 | 0.37 |

Test Description: Long-Term Experiments on Hippocampus Sections (In Vitro)

Experimental Approach

The LTP in the CA 1 region is the LTP which has been best characterized in vitro. The stratification and input structure of this region permits field potential measurements over several hours in vitro. In the NHE studies, a weak tetanus which was based on the theta rhythm and which induces an early LTP which returns to the initial value within three hours was used (Journal of Neuroscience, 18(16), 6071 (1998); Euro J. Pharmacol. 502: 99-104, 2004). It has recently been confirmed that an increasing number of theta burst trains induces an LTP of increasing magnitude and persistence (J Neurophysiol. 88:249-255, 2002), i.e. that a single weak stimulus induces an unsaturated LTP, not the maximally achievable saturated type of LTP. Both the magnitude (Behnisch, Reymann et al., Neurosci. Lett. 1998, 253(2): 91-94) and persistence (e.g. Neuropeptides 26: 421-427, 1994) of this LTP can be improved or adversely affected by substances. The early LTP which we generate in our investigations is likewise unsaturated. It is thus possible to ascertain a substance-induced improvement or deterioration in the early LTP. The early LTP investigated is composed of the STP component, which is known to persist for about 30 minutes (Nature 335: 820-824, 1988), and the LTP 1 component, which usually persists in the first 1-2 hours after LTP induction (Learn Mem. 3: 1-24, 1996).

The short (30-60 minute) recording of the initial values before the tetanus permits early effects of the substance to be investigated on normal, unstimulated synaptic transmission to be investigated. Since the principal excitatory synapses are glutamatergic (J Clin Neurophysiol. 9: 252-263, 1992), i.e. the monosynaptic field EPSP is determined very substantially by AMPA and only to a considerably smaller extent by NMDA receptors, an effect on glutamatergic transmission is thus simultaneously indirectly tested.

Method: Long-Term Experiments on Hippocampus Sections (In Vitro)

Type of animals: rats

Age: 7-8 weeks

Strain: Wistar (Shoe Wist, Shoe)

Sex: male

Breeder: Harlan Winkelmann GmbH, artificial light (6-18.00 h) and daily rhythm

Preparation:

Stunning: blow on back of neck with iron bar

Sacrifice: decapitation

Exposure of brain: cranium opened by dorsal to ventral cutting along the sagittal suture of the skull
Exposure of the hippocampus: the brain was incised between the hemispheres and, starting with the right hemisphere, the hippocampus was pulled out using a blunt implement.
Preparation of the sections: the exposed hippocampus was transferred to a cooling block with moist filter paper, and the excess moisture was drawn off with the aid of another filter paper. This hippocampus fixed to the cooling block in this way was placed on the chopper and rotated horizontally until the hippocampus was at an appropriate angle to the cutting blade.
Cutting angle: in order to maintain the laminar structure of the hippocampus it was necessary to cut the hippocampus at an angle of about 70 degrees in relation to the cutting blade (chopper).
Section: the hippocampus was sliced at intervals of 400 μm. The sections were taken off the blade with the aid of a very soft, thoroughly wetted brush (marten hair) and transferred into a glass vessel with cooled nutrient solution gassed with 95% $O_2$/5% $CO_2$. The total duration of the preparation lasted no more than 5 min.
Storage of the Sections:
Immersed section: the sections lay under a liquid level of 1-3 mm in a temperature-controlled chamber (33° C.). The flow rate was 2.5 ml/min. The pre-gassing took place under a slightly raised pressure (about 1 atm) and through a microneedle in the prechamber. The section chamber was connected to the prechamber so that it was possible to maintain a minicirculation. The minicirculation was driven by the 95% $O_2$/5% $CO_2$ flowing out through the microneedle.
Section adaptation: the freshly prepared hippocampus sections were adapted in the section chamber at 33° C. for at least 1 h.
Determination of the Test Stimulus Level:
Stimulus level: fEPSP: 30% of the maximum EPSP
Measurement of the Focal Potentials
Stimulation: a monopolar stimulation electrode consisting of lacquered stainless steel and a constant-current, biphasic stimulus generator (WPI A 365) were used for local stimulation of Schaffer collaterals (voltage: 1-5 V, pulse width of one polarity 0.1 ms, total pulse 0.2 ms).
Measurement: glass electrodes (borosilicate glass with filament, 1-5 MOhm, diameter: 1.5 mm, tip diameter: 3-20 μm) which were filled with normal nutrient solution were used to record the excitatory post-synaptic potentials (fEPSP) from the Stratum radiatum. The field potentials were measured versus a chlorinated silver reference electrode located at the edge of the section chamber using a DC voltage amplifier. The field potentials were filtered through a low-pass filter (5 kHz).
Determination of the field potentials: the slope of the fEPSPs (fEPSP slope) was determined for the statistical analysis of the experiments. The recording, analysis and control of the experiment took place with the aid of a software program (PWIN) which was developed in the department of neurophysiology. The formation of the average fEPSP slopes at the respective time points and construction of the diagrams took place with the aid of the Excel software, with automatic data recording by an appropriate macro.
Nutrient Medium (Ringer's Solution):

| Substance | in mM | for 1 l in g |
|---|---|---|
| NaCl | 124 | 7.248 |
| KCl | 4.9 | 0.356 |
| $MgSO_4$* $7H_2O$ | 1.3 | 0.321 |
| $CaCl_2$+ anhydrous | 2.5 | 0.368 |
| $KH_2PO_4$ | 1.2 | 0.164 |
| $NaHCO_3$ | 25.6 | 2.152 |
| Glucose | 10 | 1.802 |
| Osmolarity in mOsm | 330 | |
| PH | 7.4 | |

Example 1 was dissolved in DMSO and diluted with Ringer's solution to the final concentration for the experiments (final concentration 0.01% DMSO).
Outline of the Experiments:
In the control experiments, the baseline synaptic transmission was initially recorded for 60-120 minutes. Subsequently, two double pulses were administered four times at an interval of 200 ms, with an interpulse interval of 10 ms for the double pulses and a width of 0.2 ms for the individual pulses (weak tetanus). The resulting potentiation of the EPSPs was recorded for at least 60 minutes.
In the experiments to test the effect of the NHE5 inhibitor, the baseline was again recorded initially for 60-120 minutes. The NHE5 inhibitor (10 μM) was flushed in 20 minutes before the stimulation. Two double pulses were administered four times at an interval of 200 ms as in the control experiments, with an interpulse interval of 10 ms for the double pulses and a width of 0.2 ms for the individual pulses. The substance was washed out 20 minutes after stimulation, and the potentiation of the EPSP was recorded for at least 60 minutes.
Result:
The compound of example 1 had no intrinsic effect on synaptic transmission in the concentration used.
The potentiation after administration of example 1 was still 137% of the baseline 80 min after the stimulus, whereas the potentiation under control conditions had almost returned to the baseline level, at 113% of the baseline. This shows clearly that even 10 μM of the compound of example 1 improve maintenance of the weak LTP.

What is claimed is:
1. A compound of formula I

I wherein:
R1, R2, R3 and R4 are each independently selected from the group consisting of hydrogen, F, Cl, Br, I, CN, $NO_2$ and R11-$(C_mH_{2m})$-$A_n$-;
m is zero, 1, 2, 3 or 4;

n is zero or 1;
R11 is hydrogen, methyl or $C_pF_{2p+1}$;
A is oxygen, NH, N(CH$_3$) or S(O)$_q$;
p is 1, 2 or 3;
q is zero, 1 or 2;
R5 is selected from the group consisting of hydrogen, alkyl having 1, 2, 3, 4, 5 or 6 carbon atoms and cycloalkyl having 3, 4, 5 or 6 carbon atoms;
R6 is selected from the group consisting of hydrogen, OH, F, CF$_3$, alkyl having 1, 2, 3 or 4 carbon atoms and cycloalkyl having 3, 4, 5 or 6 carbon atoms;
R7 and R8 are each independently selected from the group consisting of hydrogen, F, Cl, Br, CN, CO$_2$R12, NR13R14 and R16-(C$_{mm}$H$_{2mm}$)-E$_{nn}$-;
R12 is independently selected from the group consisting of hydrogen, alkyl having 1, 2, 3 or 4 carbon atoms and cycloalkyl having 3, 4, 5 or 6 carbon atoms;
R13 and R14 are each independently selected from the group consisting of hydrogen, alkyl having 1, 2, 3 or 4 carbon atoms and cycloalkyl having 3, 4, 5 or 6 carbon atoms;
or
R13 and R14, together with the nitrogen atom to which they are bonded, form a 4-, 5-, 6- or 7-membered ring in which one CH$_2$ group may be replaced by NR15, S or oxygen;
R15 is selected from the group consisting of hydrogen, alkyl having 1, 2, 3 or 4 carbon atoms and cycloalkyl having 3, 4, 5 or 6 carbon atoms;
mm is zero, 1, 2, 3 or 4;
nn is zero or 1;
R16 is hydrogen, methyl or $C_{pp}F_{2pp+1}$;
E is oxygen or S(O)$_{qq}$;
pp is 1, 2 or 3;
qq is zero, 1 or 2;
or a pharmaceutically acceptable salt or trifluoroacetate thereof.

2. The compound of formula I as recited in claim 1 wherein
R1, R2, R3 and R4 are each independently selected from the group consisting of hydrogen, F, Cl, Br, CN and R11-(C$_m$H$_{2m}$)-A$_n$-;
m is zero or 1;
n is zero or 1;
R11 is hydrogen, methyl or $C_pF_{2p+1}$;
A is oxygen, NCH$_3$ or S(O)$_q$;
p is 1 or 2;
q is zero, 1 or 2;
R5 is hydrogen, methyl, ethyl or cyclopropyl;
R6 is hydrogen or methyl;
R7 and R8 are each independently selected from the group consisting of hydrogen, F, Cl, CN, CO$_2$R12, NR13R14 and R16-(C$_{mm}$H$_{2mm}$)-E$_{nn}$-;
R12 is hydrogen, methyl or ethyl;
R13 and R14 are each independently selected from the group consisting of hydrogen, alkyl having 1, 2, 3 or 4 carbon atoms and cycloalkyl having 3, 4, 5 or 6 carbon atoms;
or
R13 and R14, together with the nitrogen atom to which they are bonded, form a 5-, 6- or 7-membered ring in which one CH$_2$ group may be replaced by NR15, S or oxygen;
R15 is selected from the group consisting of hydrogen, alkyl having 1, 2, 3 or 4 carbon atoms and cycloalkyl having 3, 4, 5 or 6 carbon atoms;
mm is zero, 1 or 2;
nn is zero or 1;
R16 is hydrogen, methyl or $C_{pp}F_{2pp+1}$;
E is oxygen or S(O)$_{qq}$;
pp is 1 or 2;
qq is zero, 1 or 2;
or a pharmaceutically acceptable salt or trifluoroacetate thereof.

3. The compound of the formula I as recited in claim 2, in which
R1 and R3 are each hydrogen;
R2 and R4 are each independently selected from the group consisting of hydrogen, F, Cl, NH$_2$, NHCH$_3$ and N(CH$_3$)$_2$;
R5 is hydrogen, methyl, ethyl or cyclopropyl;
R6 is hydrogen or methyl;
R7 and R8 are each hydrogen;
or a pharmaceutically acceptable salt or trifluoroacetate thereof.

4. The compound of the formula I or a pharmaceutically acceptable salt thereof as recited in claim 3 formulated as a pharmaceutical composition.

5. A pharmaceutical composition comprising the compound of the formula I or a pharmaceutically acceptable salt thereof as recited in claim 3 for the treatment of disorders of respiratory drive, respiratory disorders, sleep-related respiratory disorders, sleep apneas, of snoring, of acute and chronic renal disorders, of acute kidney failure and of chronic kidney failure, of disorders of intestinal function, of high blood pressure, of essential hypertension, of disorders of the central nervous system, of disorders resulting from CNS overexcitability, epilepsy and centrally induced convulsions or of states of anxiety, depressions and psychoses, of ischemic states of the peripheral or central nervous system or of stroke, of acute and chronic damage to and disorders of peripheral organs or limbs caused by ischemic events or by reperfusion events, of atherosclerosis, of disorders of lipid metabolism, of thromboses, of disorders of biliary function, of infestation by ectoparasites, of disorders caused by endothelial dysfunction, of protozoal disorders, of malaria, for the preservation and storage of transplants for surgical procedures, for use in surgical operations and organ transplants, for use in bypass operations, in resuscitation after cardiac arrest, or for the treatment of states of shock or of diabetes and late damage from diabetes, or of diseases in which cellular proliferation constitutes a primary or secondary cause.

6. The pharmaceutical composition comprising the compound of formula I or a pharmaceutically acceptable salt thereof as recited in claim 3 in combination with one or more other therapeutically effective active ingredients for the treatment or prophylaxis of disorders of respiratory drive, of respiratory disorders, sleep-related respiratory disorders, sleep apneas, of snoring, of acute and chronic renal disorders, of acute kidney failure and of chronic kidney failure, of disorders of intestinal function, of high blood pressure, of essential hypertension, of disorders of the central nervous system, of disorders resulting from CNS overexcitability, epilepsy and centrally induced convulsions or of states of anxiety, depressions and psychoses, of ischemic states of the peripheral or central nervous system or of stroke, of acute and chronic damage to and disorders of peripheral organs or limbs caused by ischemic events or by reperfusion events, of atherosclerosis, of disorders of lipid metabolism, of thromboses, of disorders of biliary function, of infestation by ectoparasites, of disorders caused by endothelial dysfunction, of protozoal disorders, of malaria, for the preservation and storage of transplants for surgical procedures, for use in surgical operations and organ transplants, for use in bypass operations, in resuscitation after cardiac arrest, or for the treatment of states of shock or of diabetes and late damage from diabetes, or of diseases in which cellular proliferation constitutes a primary or secondary cause.

7. The pharmaceutical composition comprising the compound of formula I or a pharmaceutically acceptable salt thereof as recited in claim 3 in combination with one or more other therapeutically effective active ingredients for the treatment of disorders of respiratory drive and of sleep-related respiratory disorders.

8. The pharmaceutical composition of claim 7 wherein said respiratory drive and/or of sleep-related respiratory disorder is sleep apnea or snoring.

9. A method for the treatment of disorders of respiratory drive and/or of sleep-related respiratory disorders comprising the administration of a compound of formula I or its pharmaceutically acceptable salts as recited in claim 3 alone or in combination with other therapeutically effective pharmaceutical actives and acceptable excipients to a patient in need thereof.

10. The method of claim 8 wherein said sleep-related respiratory disorder is sleep apnea or snoring.

11. A method for the treatment of acute or chronic renal disorders, kidney failure or chronic kidney failure comprising the administration of a compound of formula I or its pharmaceutically acceptable salts as recited in claim 3 alone or in combination with other therapeutically effective pharmaceutical actives and acceptable excipients to a patient in need thereof.

12. A method for the treatment of disorders of intestinal function comprising the administration of a compound of formula I or its pharmaceutically acceptable salts as recited in claim 3 alone or in combination with other therapeutically effective pharmaceutical actives and acceptable excipients to a patient in need thereof.

13. A method for the treatment of disorders of the central nervous system comprising the administration of a compound of formula I or its pharmaceutically acceptable salts as recited in claim 3 alone or in combination with other pharmaceutical actives and acceptable excipients to a patient in need thereof.

14. A pharmaceutical preparation for human, veterinary or phytoprotective use, comprising an effective amount of a compound of the formula I or of a pharmaceutically acceptable salt thereof as recited in claim 3.

15. A pharmaceutical preparation for human, veterinary or phytoprotective use, comprising an effective amount of a compound of the formula I and/or of a pharmaceutically acceptable salt thereof as recited in claim 3 in combination with other pharmacological active ingredients or excipients.

* * * * *